US012714293B2

(12) United States Patent
Kobayashi et al.

(10) Patent No.: US 12,714,293 B2
(45) Date of Patent: Aug. 25, 2026

(54) MEDICAL OBSERVATION SYSTEM, METHOD, AND MEDICAL OBSERVATION DEVICE

(71) Applicant: Sony Group Corporation, Tokyo (JP)

(72) Inventors: Yohei Kobayashi, Tokyo (JP); Yoshio Soma, Tokyo (JP); Keisuke Uyama, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 18/988,944

(22) Filed: Dec. 20, 2024

(65) Prior Publication Data

US 2025/0127382 A1 Apr. 24, 2025

Related U.S. Application Data

(63) Continuation of application No. 17/441,698, filed as application No. PCT/JP2020/012676 on Mar. 23, 2020, now Pat. No. 12,207,794.

(30) Foreign Application Priority Data

Mar. 29, 2019 (JP) ................................ 2019-065756

(51) Int. Cl.
*A61B 1/00* (2006.01)
*A61B 34/30* (2016.01)
(Continued)

(52) U.S. Cl.
CPC ...... *A61B 1/00188* (2013.01); *A61B 1/00045* (2013.01); *A61B 1/00149* (2013.01);
(Continued)

(58) Field of Classification Search
None
See application file for complete search history.

(56) References Cited

U.S. PATENT DOCUMENTS

2015/0235373 A1 8/2015 Kato et al.
2015/0272422 A1 10/2015 Aoyama
(Continued)

FOREIGN PATENT DOCUMENTS

EP 2926718 A1 10/2015
JP 11-337845 A 12/1999
(Continued)

OTHER PUBLICATIONS

International Search Report and Written Opinion mailed on Jun. 9, 2020, received for PCT Application No. PCT/JP2020/012676, Filed on Mar. 23, 2020, 9 pages.

*Primary Examiner* — Samira Monshi
(74) *Attorney, Agent, or Firm* — XSENSUS LLP

(57) ABSTRACT

The present technology relates to a medical observation system, a method, and a medical observation device, which are capable of maintaining accuracy of three-dimensional information, even in a case where a change occurs in an optical system. A medical observation system acquires operative field data acquired by a medical observation device, detects a change in an optical system of the medical observation device, estimates a parameter representing a state of the optical system after a change occurs in the optical system in a case where the change in the optical system is detected, and sets a generation condition of three-dimensional information based on the operative field data by using an estimation result. The present technology can be applied to a surgery assisting system.

20 Claims, 10 Drawing Sheets

(51) Int. Cl.
*G02B 21/00* (2006.01)
*G02B 21/36* (2006.01)
*G02B 23/24* (2006.01)

(52) U.S. Cl.
CPC .......... *A61B 1/00193* (2013.01); *A61B 34/30* (2016.02); *G02B 21/0012* (2013.01); *G02B 21/365* (2013.01); *G02B 23/2484* (2013.01)

(56) References Cited

U.S. PATENT DOCUMENTS

| | | | | |
|---|---|---|---|---|
| 2016/0270757 | A1* | 9/2016 | Toma | A61B 8/5223 |
| 2017/0020627 | A1 | 1/2017 | Tesar et al. | |

FOREIGN PATENT DOCUMENTS

| | | | |
|---|---|---|---|
| JP | 2009-258273 | A | 11/2009 |
| JP | 2010-263949 | A | 11/2010 |
| JP | 2015-195844 | A | 11/2015 |
| JP | 2017-225700 | A | 12/2017 |
| JP | 2018-161377 | A | 10/2018 |
| WO | 2018/179749 | A1 | 10/2018 |

* cited by examiner

1
CCU
LIGHT SOURCE DEVICE
TREATMENT TOOL DEVICE
INSUFFLATION DEVICE
RECORDER
PRINTER
15
13
17
21
24
26
27
31
11
22
23
25a
25b
25b
U
33
35

FIG. 6

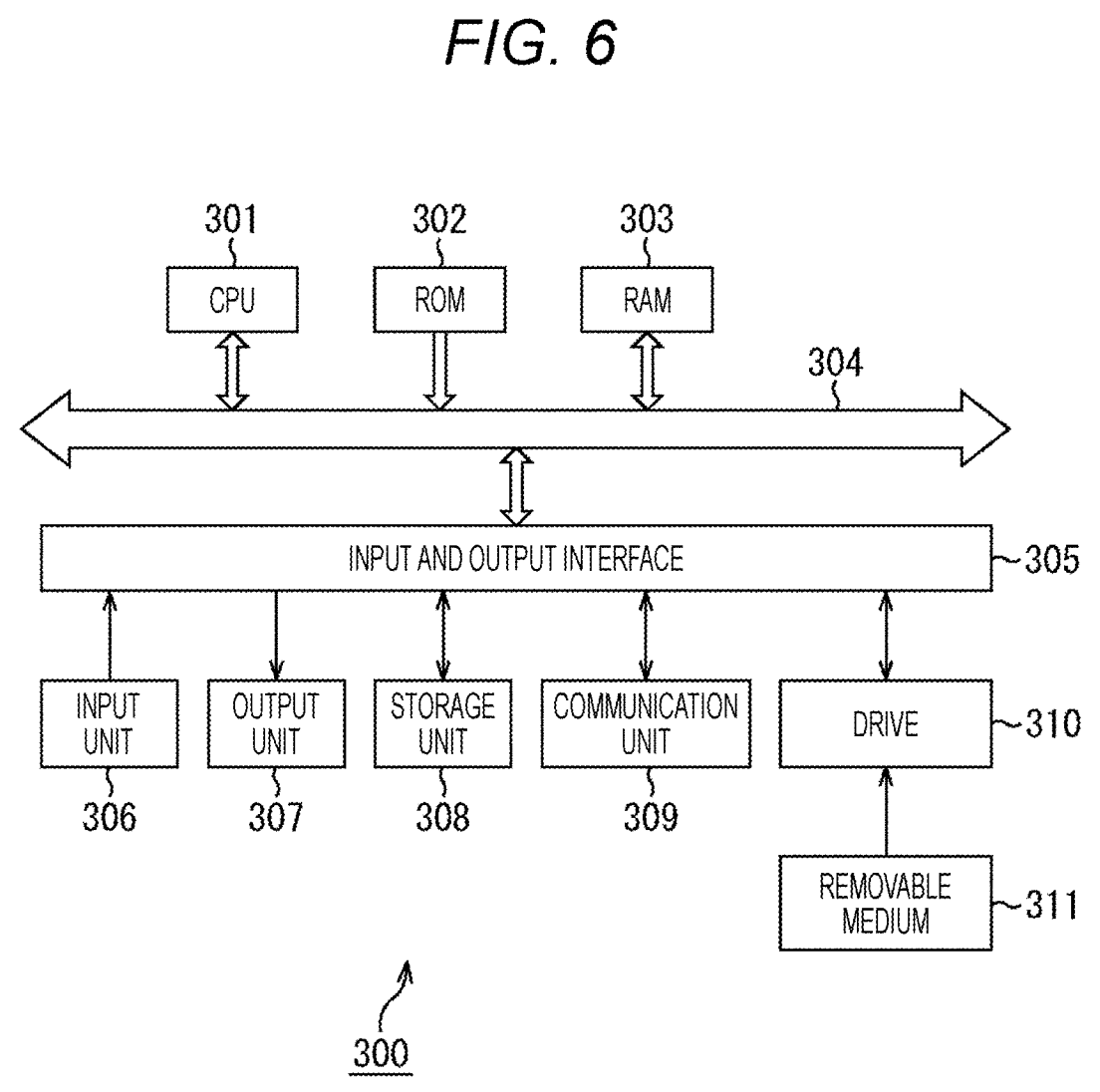

301 CPU
302 ROM
303 RAM
304
305 INPUT AND OUTPUT INTERFACE
306 INPUT UNIT
307 OUTPUT UNIT
308 STORAGE UNIT
309 COMMUNICATION UNIT
310 DRIVE
311 REMOVABLE MEDIUM
300

Figure 10:
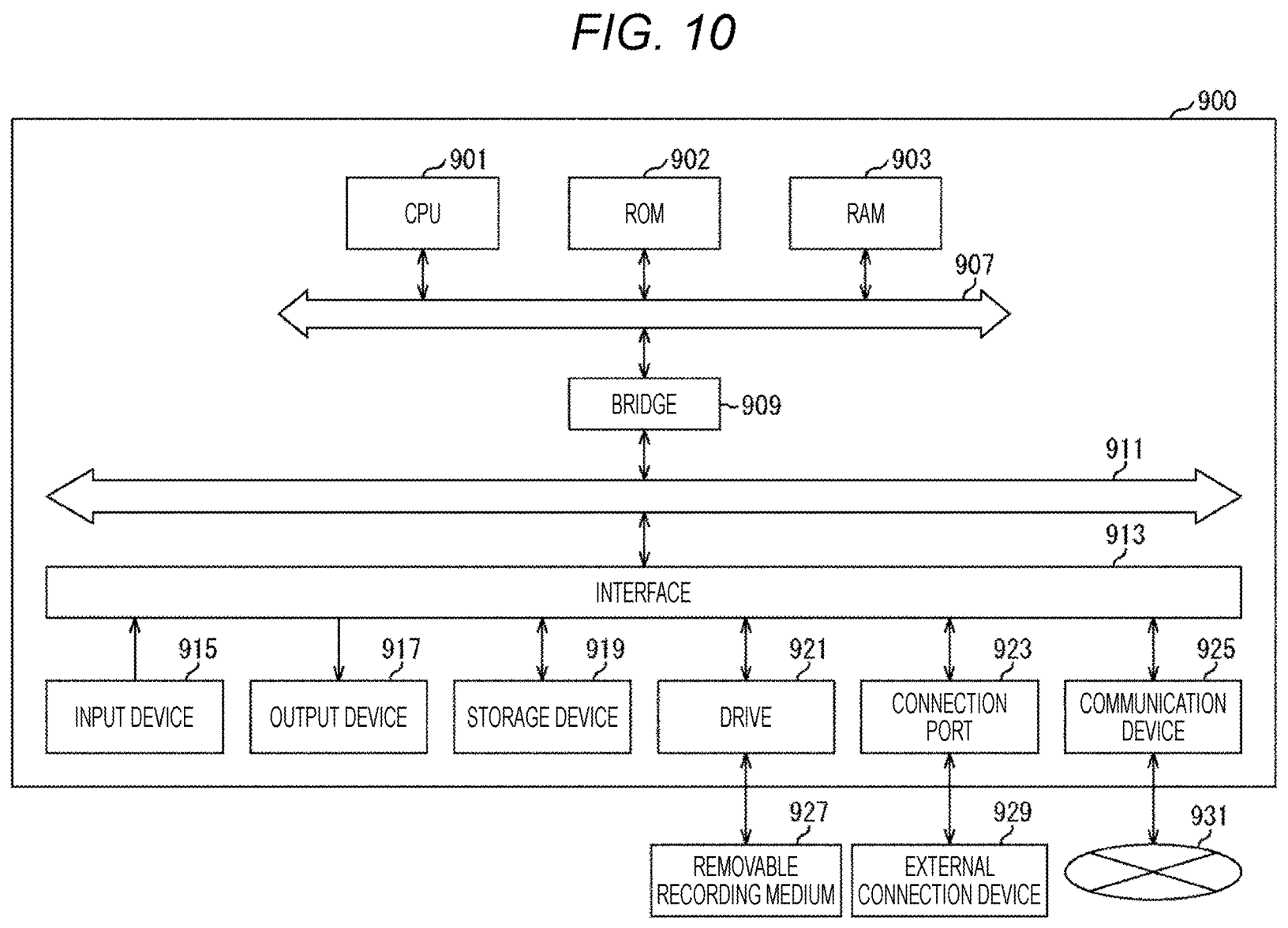

900
901 CPU
902 ROM
903 RAM
907
909 BRIDGE
911
913 INTERFACE
915 INPUT DEVICE
917 OUTPUT DEVICE
919 STORAGE DEVICE
921 DRIVE
923 CONNECTION PORT
925 COMMUNICATION DEVICE
927 REMOVABLE RECORDING MEDIUM
929 EXTERNAL CONNECTION DEVICE
931

MEDICAL OBSERVATION SYSTEM, METHOD, AND MEDICAL OBSERVATION DEVICE

CROSS-REFERENCE TO RELATED APPLICATIONS

The present application is a continuation of U.S. application Ser. No. 17/441,698, filed Sep. 22, 2021, which is based on PCT filing PCT/JP2020/012676, filed Mar. 23, 2020, which claims priority to JP 2019-065756, filed Mar. 29, 2019, the entire contents of each are incorporated herein by reference.

TECHNICAL FIELD

The present technology relates to a medical observation system, a method, and a medical observation device, and more particularly, to a medical observation system, a method, and a medical observation device, which are capable of maintaining accuracy of three-dimensional information, even in a case where a change occurs in an optical system.

BACKGROUND ART

In surgery using a medical observation device such as an endoscope or a microscope, it has been proposed that three-dimensional information is generated on the basis of an operative field image, and the three-dimensional information is used for image processing or display processing of the operative field image.

For example, Patent Document 1 proposes a technique of generating three-dimensional information by SLAM and performing a display on a screen.

CITATION LIST

Patent Document

Patent Document 1: Japanese Patent Application Laid-Open No. 2017-225700

SUMMARY OF THE INVENTION

Problems to be Solved by the Invention

Incidentally, there is a case where the optical system of the medical observation device is changed during the surgery. For example, in a case where focus adjustment of the medical observation device is performed, a position of a focus lens in the optical system is moved. In particular, in endoscopic surgery, a scope of the endoscope may be replaced during the surgery, which causes a change in the optical system.

In a case where the optical system of the medical observation device is changed, the assumed parameter is different. Therefore, the accuracy of the three-dimensional information generated before the change is different from the accuracy of the three-dimensional information generated after the change. However, it is difficult to recreate the three-dimensional information from the beginning during the surgery.

The present technology has been made in view of such a situation, and an object thereof is to maintain the accuracy of three-dimensional information even in a case where a change occurs in the optical system.

Solutions to Problems

According to an aspect of the present technology, there is provided a medical observation system including: an acquisition unit configured to acquire operative field data acquired by a medical observation device; a detection unit configured to detect a change in an optical system of the medical observation device; an estimation unit configured to estimate a parameter determined depending on the optical system after a change occurs in the optical system in a case where the change in the optical system is detected by the detection unit; and a setting unit configured to set a generation condition of three-dimensional information based on the operative field data by using an estimation result of the estimation unit.

According to another aspect of the present technology, there is provided a medical observation device including: an imaging unit configured to image an operative field and generate operative field data; and an output unit configured to output the operative field data, the medical observation device being used in a medical observation system in which a change in an optical system of the imaging unit is detected, in a case where a change in the optical system is detected, a parameter determined depending on the optical system after the change is estimated, and a generation condition of three-dimensional information based on the operative field data is set by using an estimation result.

In the present technology, the operative field data acquired by the medical observation device is acquired, a change in an optical system of the medical observation device is detected, in a case where a change in the optical system is detected, a parameter determined depending on the optical system after the change is estimated, and a generation condition of three-dimensional information based on the operative field data is set by using an estimation result.

BRIEF DESCRIPTION OF DRAWINGS

FIG. 6 is a diagram illustrating a configuration example of an information processing device configuring a surgery assisting system according to a second embodiment of the present technology.

FIG. 9 is a diagram illustrating another configuration example of a surgery assisting system according to an embodiment of the present technology.

FIG. 10 is a block diagram illustrating a hardware configuration example of an information processing device.

MODE FOR CARRYING OUT THE INVENTION

Hereinafter, modes for carrying out the present technology will be described. A description will be given in the following order.

1. First embodiment (Use during surgery)
2. Second embodiment (Use in training)
3. Application example
4. Hardware configuration
5. Others

1. First Embodiment (Use During Surgery)

<Configuration Example of Surgery Assisting System (Example in which Endoscope is Held by Scopist)>

Figure 1:
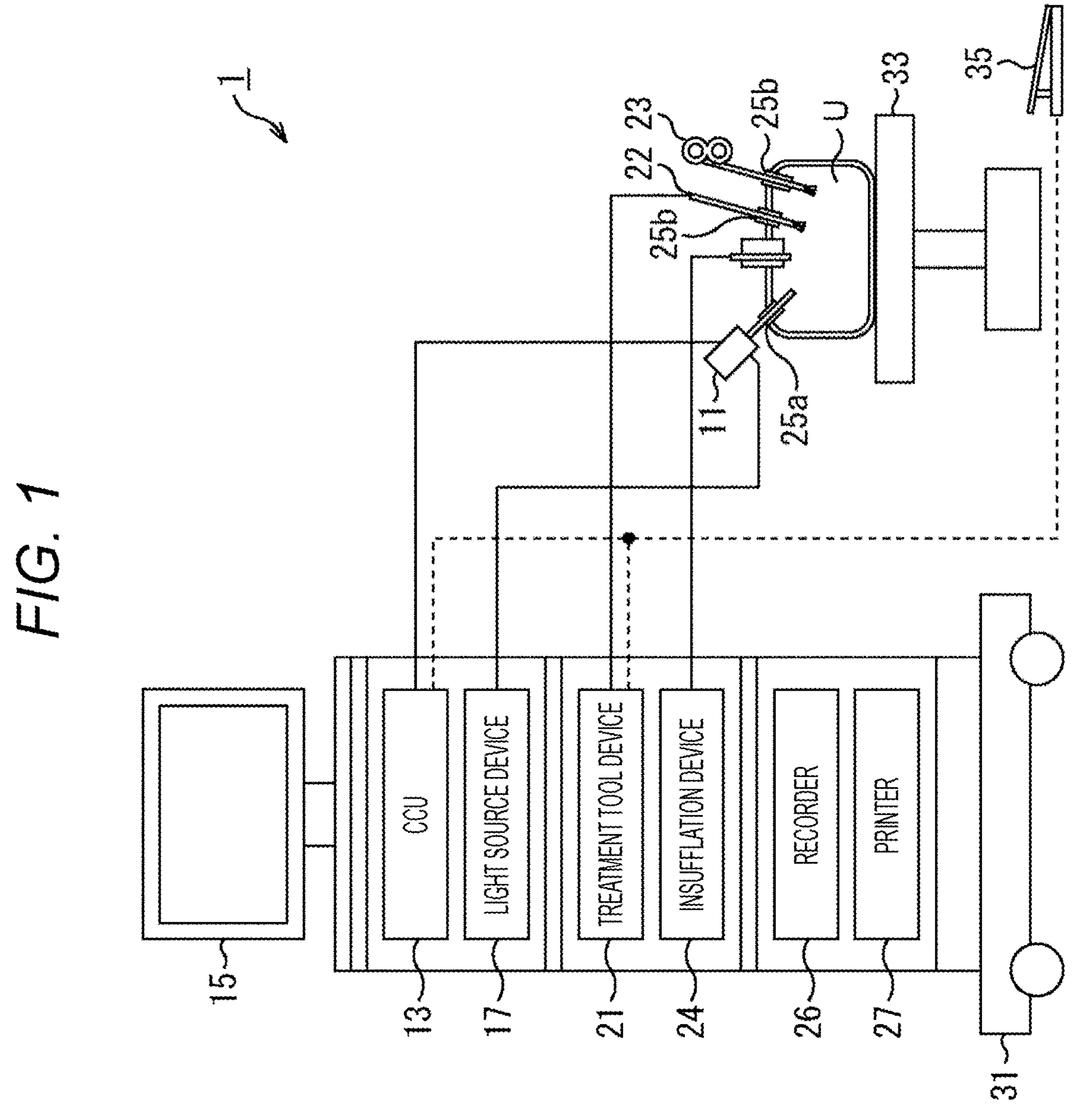
FIG. 1 is a diagram illustrating a configuration example of a surgery assisting system according to a first embodiment of the present technology.

FIG. 1 is a diagram illustrating a configuration example of a surgery assisting system according to a first embodiment of the present technology.

For example, FIG. 1 illustrates an example of an endoscopic surgery system used in endoscopic surgery on an abdomen, which is performed in place of a laparotomy of the related art in a medical site.

In the surgery assisting system 1 of FIG. 1, in the endoscopic surgery of the abdomen, instead of incising the abdominal wall to open the abdomen as in the related art, hole-opening instruments called trocars 25*a* and 25*b* punctures the abdominal wall at several places. Then, a laparoscope (hereinafter, also referred to as an endoscope) 11 as an observation medical device for observing an inside of a patient's body, an energy treatment tool 22, a forceps 23, and the like are inserted into the body through holes provided in the trocars 25*a* and 25*b*.

While observing an image of an affected site (tumor or the like) U inside the patient's body, which is captured by the endoscope 11 in real time, an operator performs treatment such as excision of the affected site U with the energy treatment tool 22 or the like. The endoscope 11, the energy treatment tool 22, and the forceps 23 are held by an operator, a robot, or the like. Note that, the operator is referred to as a medical worker involved in surgery performed in an operation room, and the operator includes, for example, a medical doctor who is monitoring the surgery from a place different from the operating room in addition to an operating surgeon, an assistant, a scopist, and a nurse. In the example of FIG. 1, the endoscope 11 is held by, for example, the scopist. The endoscope 11 includes a scope inserted into a patient and a camera head including an imaging element that receives and images light guided by the scope. Note that, the scope may be rigid or flexible. Furthermore, the scope and the imaging element may be integrated.

In an operation room in which such endoscopic surgery is performed, a cart 31 on which devices for the endoscopic surgery are mounted, a patient bed 33 on which a patient lies down, a foot switch 35, and the like are installed. For example, devices such as a camera control unit (CCU) 13, a light source device 17, a treatment tool device 21, an insufflation device 24, a display device 15, a recorder 26, and a printer 27 are placed on the cart 31 as medical devices.

An image signal of the affected site U imaged through an observation optical system of the endoscope 11 is transmitted to the CCU 13 via a camera cable which is a signal transmission cable. The CCU 13 may be connected to the endoscope 11 via a wireless communication path in addition to being connected to the endoscope 11 via the camera cable. The CCU 13 performs signal processing on the image signal output from the endoscope 11, and outputs the image signal obtained after the signal processing to the display device 15. In such a configuration, an operative field image of the affected site U is displayed on the display device 15.

Note that, the CCU 13 may cause the recorder 26 to record the operative field image of the affected site U as image data (for example, data of a moving image) by outputting the image signal obtained after the signal processing to the recorder 26. Furthermore, the CCU 13 may cause the printer 27 to print the operative field image of the affected site U by outputting the image signal obtained after the signal processing to the printer 27.

The light source device 17 is connected to the endoscope 11 via a light guide cable, and can switch light of various wavelengths to radiate the light to the affected site U. The light radiated from the light source device 17 may be used as, for example, auxiliary light.

The treatment tool device 21 corresponds to, for example, a high frequency output device that outputs a high frequency current to the energy treatment tool 22 that cuts off the affected site U by using electric heat.

The insufflation device 24 includes air supply means and air suction means, and supplies air to, for example, an abdominal region in the patient's body.

The foot switch 35 controls the CCU 13, the treatment tool device 21, and the like by using a foot operation of an operator, an assistant, or the like as a trigger signal.

<Functional Configuration Example of Surgery Assisting System>

(Configuration Around CCU 13)

Figure 2:
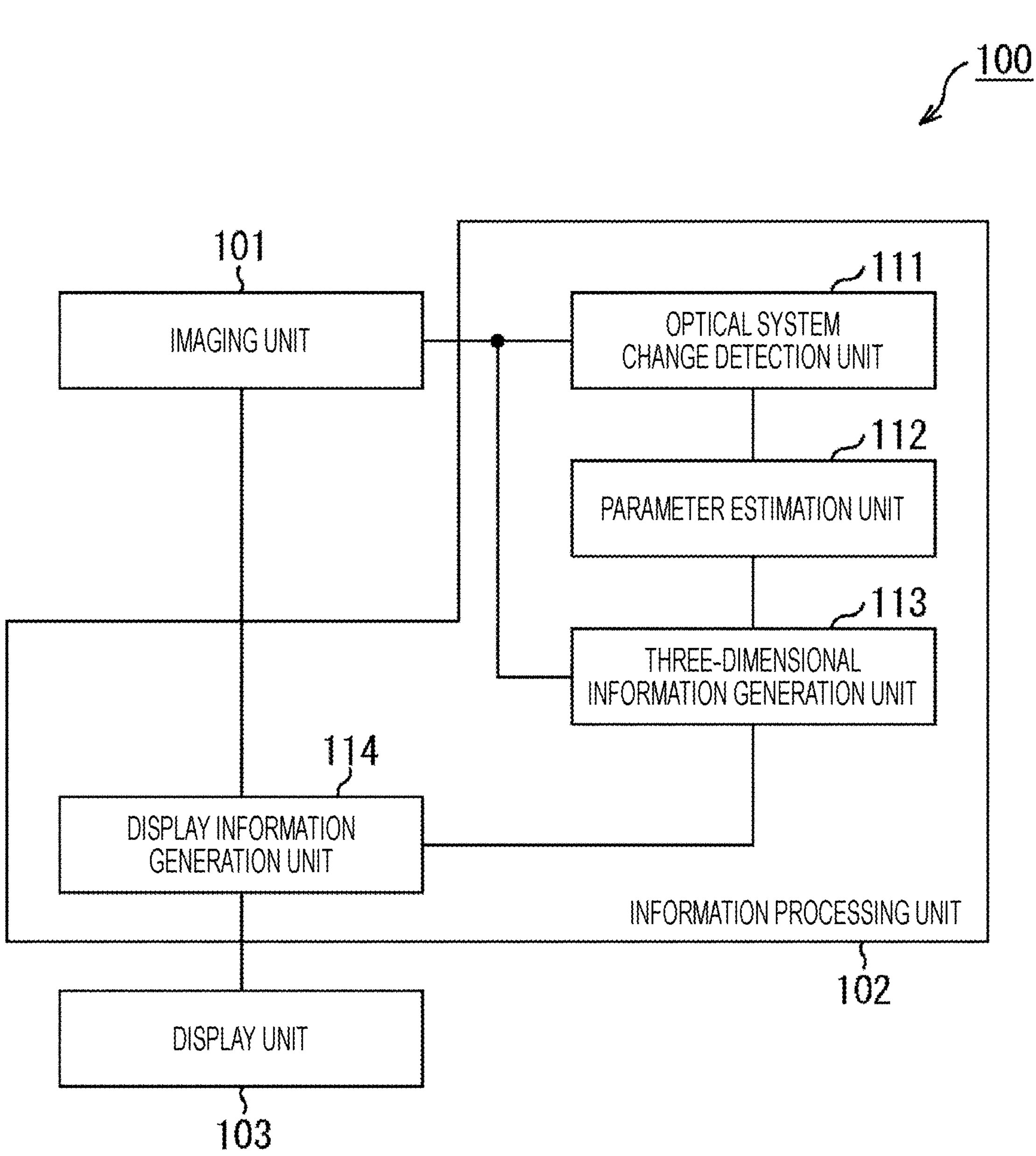
FIG. 2 is a block diagram illustrating a functional configuration example of a surgery assisting system according to a first embodiment of the present technology.

FIG. 2 is a block diagram illustrating a functional configuration example of the surgery assisting system.

A surgery assisting system 100 in FIG. 2 includes an imaging unit 101, an information processing unit 102, and a display unit 103.

The imaging unit 101 corresponds to the endoscope 11 in FIG. 1. The imaging unit 101 images an operative field according to the operation by the scopist, and outputs an image signal obtained by the imaging to the information processing unit 102. The imaging unit 101 is a medical observation device that outputs operative field data obtained by imaging the operative field. As the medical observation device, a microscope may be used instead of the endoscope. Note that, a circuit (for example, a central processing unit (CPU), a random access memory (RAM), a read only memory (ROM), or a field-programmable gate array (FPGA)) for performing imaging processing and processing a generated image signal is stacked in the medical observation device.

The information processing unit 102 corresponds to the CCU 13 in FIG. 1. The information processing unit 102 acquires an image signal supplied from the imaging unit 101, performs signal processing on the image signal, and outputs a signal of an operative field image generated by performing the signal processing to the display unit 103. Note that, the information processing unit 102 may be constituted in a device other than the CCU 13.

The display unit 103 corresponds to the display device 15 in FIG. 1. The display unit 103 displays the operative field image on the basis of the image signal supplied from the information processing unit 102.

(Detailed Configuration of Information Processing Unit 102)

The information processing unit 102 includes an optical system change detection unit 111, a parameter estimation unit 112, a three-dimensional information generation unit 113, and a display information generation unit 114.

At least a part of the information processing unit 102 is realized by a circuit including a CPU, and the like of the CCU 13 in FIG. 1, the circuit executing a predetermined program. The image signal output from the imaging unit 101 is input to the optical system change detection unit 111, the three-dimensional information generation unit 113, and the display information generation unit 114. Note that, at least a part of the functions of the information processing unit 102 may be implemented by the FPGA.

Optical System Change Detection Unit 111

The optical system change detection unit 111 detects a change in the optical system, which occurs in the imaging unit 101 during surgery. The change in the optical system occurs, for example, in a case where an adjustment of the optical system such as an adjustment of a zoom (angle of view) (movement of a zoom lens) or an adjustment of a focus (movement of a focus lens) is performed by the imaging unit 101, in a case where the scope is replaced when the scope is included in the imaging unit 101, or the like.

Case where Information of Optical System can be Electronically Obtained from Imaging Unit 101

For example, since some optical members of the optical system included in the imaging unit 101 are moved on the basis of the output of the CCU 13 in the adjustment of the zoom and the adjustment of the focus, information (for example, information indicating a position of the zoom lens and a position of the focus lens) indicating the change in the optical system is stored in the CCU 13. In this case, the optical system change detection unit 111 detects the change in the optical system on the basis of the information indicating the change in the optical system, which is stored in the CCU 13.

Furthermore, there is a case where the imaging unit 101 includes a detachable scope, and a storage unit, which stores information indicating a type of the scope, is provided in the scope. At this time, a circuit included in the imaging unit 101 may acquire information of the scope and output the information of the scope to the CCU 13. In this case, the optical system change detection unit 111 detects the change in the optical system on the basis of the information obtained from the imaging unit 101.

Case where Information of Optical System Cannot be Electronically Obtained from Imaging Unit 101

In this case, the optical system change detection unit 111 detects a change in the optical system on the basis of the image signal obtained from the imaging unit 101.

Figure 3:
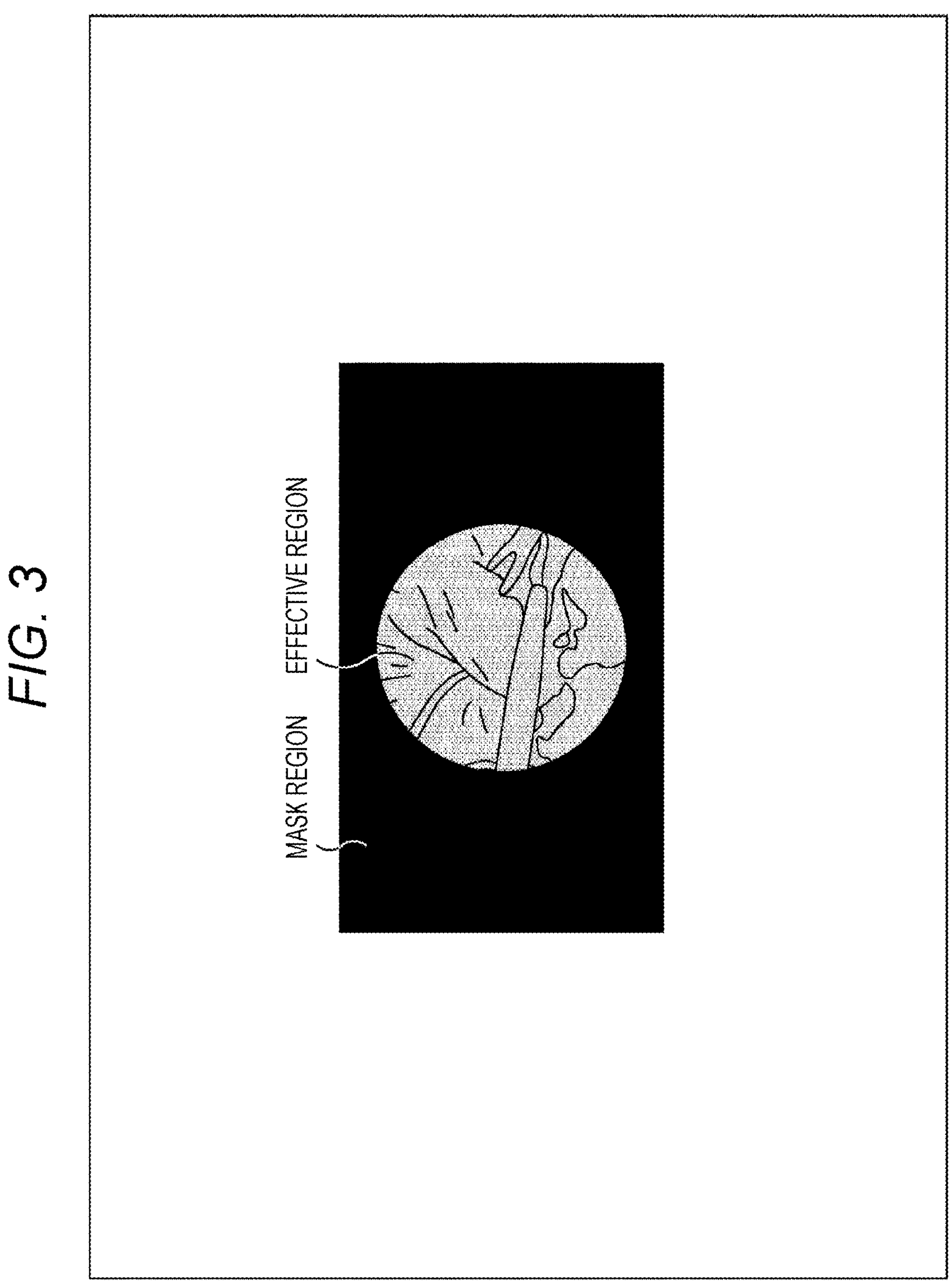
FIG. 3 is a view illustrating an example of a mask region.

For example, the optical system change detection unit 111 repeatedly detects a mask region in the image signal sequentially supplied from the imaging unit 101. As illustrated in FIG. 3, in the operative field image generated from the image signal, the mask region is a vignetting region formed around an effective region where the operative field appears. When replacement of the scope or the like is performed, the vignetting is changed, so that the mask region is changed, and a diameter of the circular effective area is changed.

The optical system change detection unit 111 detects a change in the optical system, which occurs in the imaging unit 101, by detecting such a change in the mask region.

Furthermore, the optical system change detection unit 111 detects a change in the optical system, which occurs in the imaging unit 101, by using a singular value of a camera matrix (basic matrix of a frame). It is possible to detect a change in a focal length on the basis of the singular value of the camera matrix. Therefore, it is possible to detect a change in the optical system such as a movement of the focus lens or a movement of the zoom lens.

Here, a detection method using the singular value of the camera matrix is a method of detecting, with a ratio of the singular values of the basic matrix, a change in the focal length by using a property that non-zero singular values of the basic matrix, which are calculated at two viewpoints, are the same, in a case where the focal length is the same. The method is described in, for example, "Kazuki Nozawa, "Stabilization of three-dimensional restoration for input image group with unknown focal length", CVIM-182, vol. 2012, No. 19".

Specifically, the following processing (a) to (d) are performed in the optical system change detection unit 111.

(a) The optical system change detection unit 111 records a key frame serving as a reference for generating three-dimensional information in SLAM.

(b) The optical system change detection unit 111 sequentially calculates a basic matrix E by using the key frame.

(c) The optical system change detection unit 111 calculates a non-zero singular value of the basic matrix E.

Here, the basic matrix E is a 3×3 matrix. In a case where an epipolar condition, which is the basis of three-dimensional restoration, is satisfied, a singular value of the third row of a diagonal matrix Σ when E is subjected to singular value decomposition (following equation (1)) is zero, and a diagonal matrix $\Sigma_i$ in a frame i is as in the following equation (2).

[Mathematical formula 1]

$$E = \bigcup \sum V^T \quad (1)$$

[Mathematical formula 2]

$$\sum_i = \begin{bmatrix} \sigma_{i1} & 0 & 0 \\ 0 & \sigma_{i2} & 0 \\ 0 & 0 & 0 \end{bmatrix} (\sigma_{i2} < \sigma_{i1}) \quad (2)$$

Here, $\sigma_{i2} < \sigma_{i1}$.

(d) The optical system change detection unit 111 detects a change in a focal length by comparing ratios of the non-zero singular values at each time.

That is, in a case where the calculation is performed on the basis of the images captured at the same focal length, a singular value in the first row is equal to a singular value in the second row. From this property, in a case where $\sigma_{i2}/\sigma_{i1}$ is smaller than 1, it means that the focal length has changed. Therefore, as shown in the following equation (3), a change in the optical system can be detected by comparing the ratio of the singular values of the diagonal matrix Σ in the frame i with a threshold th.

[Mathematical formula 3]

$$th < \frac{\sigma_{i2}}{\sigma_{i1}} \leq 1 \text{ ...There is no change in an optical system} \quad (3)$$

$$0 < \frac{\sigma_{i2}}{\sigma_{i1}} \leq th \text{ ...There is a change in an optical system}$$

As described above, the optical system change detection unit 111 outputs a detection result obtained by detecting the change in the optical system to the parameter estimation unit 112. The detection result output to the parameter estimation unit 112 also includes information on the optical system of the imaging unit 101. Note that, the method of detecting a change in the optical system is not limited to the method described above, and other methods can be adopted.

Parameter Estimation Unit 112

The parameter estimation unit 112 in FIG. 2 estimates a parameter serving as a generation condition of three-dimensional information based on the operative field image. The parameter is a parameter determined depending on the optical system, and is, for example, information indicating a focal length, an image center, a magnification, and a lens distortion coefficient. The information configuring the parameter is only required to include at least one parameter determined depending on the optical system, and is only required to include at least one of, for example, a focal length, an image center, a magnification, or a distortion coefficient. Note that, the parameter determined depending on the optical system includes a parameter determined depending on an arrangement of the optical system in the imaging unit 101. For example, even for the same scope, an image center may be slightly changed by removing the scope.

Case where Information of Optical System can be Electronically Obtained from Imaging Unit 101

In this case, the parameter estimation unit 112 refers to a table representing a relationship between information of the optical system and a parameter, and obtains a parameter corresponding to the information of the optical system, the information obtained from the imaging unit 101. A table, which is generated in advance and represents a relationship between information of the optical system and a parameter, is provided to the parameter estimation unit 112.

Case where Information of Optical System Cannot be Electronically Obtained from Imaging Unit 101

In this case, the parameter estimation unit 112 estimates a parameter matrix as a parameter on the basis of the image signal obtained from the imaging unit 101.

For example, an estimation method, which applies Self-Calibration capable of estimating a matrix of parameters without using a calibration pattern, is used. Self-Calibration is described in, for example, "O. D. Faugeras, "Camera self-calibration: Theory and experiments", Europe Conference on Computer Vision, 1992, pp 321-334.". The parameter estimation unit 112 calculates information serving as a reliability index of the estimated parameter matrix.

The parameter estimation unit 112 determines whether or not to newly set a generation condition of the three-dimensional information, that is, whether or not to update, with the estimated parameter, the parameter serving as the generation condition of the three-dimensional information by using the estimation result of the parameter. In a case where the parameter serving as the generation condition of the three-dimensional information is determined to be updated, the parameter serving as the generation condition of the three-dimensional information is updated.

As a method of determining whether or not to update the parameter, there are an automatic determination method in which the parameter estimation unit 112 performs a determination by itself, and a manual determination method in which a user causes the determination to be performed.

In the case of using the automatic determination method, the parameter estimation unit 112 determines whether or not to update the parameter according to a threshold determination using the reliability index of the parameter matrix obtained after the estimation. For example, in a case where the reliability index of the parameter matrix obtained after the estimation is higher than a preset threshold, it is determined that the parameter is updated, and in a case where the reliability index is lower than the threshold, it is determined that the parameter is not updated.

In the case of using the manual determination method, the parameter estimation unit 112 presents the estimation result on the display unit 103, and determines whether or not to update the parameter according to selection of the user who has seen the estimation result.

Three-Dimensional Information Generation Unit 113

The three-dimensional information generation unit 113 generates three-dimensional information by using a parameter serving as a generation condition of the three-dimensional information on the basis of each frame of the operative field image represented by the image signal supplied from the imaging unit 101. The three-dimensional information is information generated by using the above-described parameters on the basis of the operative field image. The three-dimensional information includes a three-dimensional map representing a three-dimensional structure of a subject (in an organ or a body cavity) appearing in the operative field image, and position and orientation information representing a self-position and orientation of the imaging unit 101.

As an algorithm for a three-dimensional information generation, Visual SLAM in which only an operative field image is input, RGB-D-SLAM in which depth information is measured by a ToF sensor, Lidar, or the like and the operative field image and the depth information are input, or the like is used.

In a case where a change in the optical system is detected by the optical system change detection unit 111, the three-dimensional information generation unit 113 stops generating the three-dimensional information until a new parameter is estimated by the parameter estimation unit 112. In a case where the new parameter is estimated, the three-dimensional information generation unit 113 resumes the generation of the three-dimensional information by using the new parameter.

Furthermore, in a case where a change in the optical system is detected by the optical system change detection unit 111, the three-dimensional information generation unit 113 stores the three-dimensional information by distinguishing between the three-dimensional information before the change in the optical system and the three-dimensional information after the change in the optical system without stopping the generation of the three-dimensional information. When the same place as the place imaged before the change in the optical system is imaged after the new parameter is estimated, the three-dimensional information generation unit 113 updates the three-dimensional information by replacing the three-dimensional information of the place (three-dimensional information before the change in the optical system) with three-dimensional information generated by using the new parameter (three-dimensional information after the change of the optical system).

The three-dimensional information generation unit 113 outputs the three-dimensional information generated in this manner to the display information generation unit 114.

Display Information Generation Unit 114

The display information generation unit 114 causes the display unit 103 to display the operative field image on the basis of the image signal supplied from the imaging unit 101.

Furthermore, the display information generation unit 114 causes the display unit 103 to display the three-dimensional map on the basis of the three-dimensional information supplied from the three-dimensional information generation unit 113. The three-dimensional map may be displayed by changing a display method for color or the like before and after the parameter is updated.

Furthermore, the display information generation unit 114 displays the detection result of the change in the optical system in the optical system change detection unit 111. At that time, information indicating that the scope in the imaging unit 101 has been replaced may be displayed, or information such as a type of the scope after the replacement may be displayed.

Moreover, the display information generation unit 114 may cause the display unit 103 to display a new parameter set as a generation condition of the three-dimensional information.

<Operation Example of Surgery Assisting System>

Figure 4:
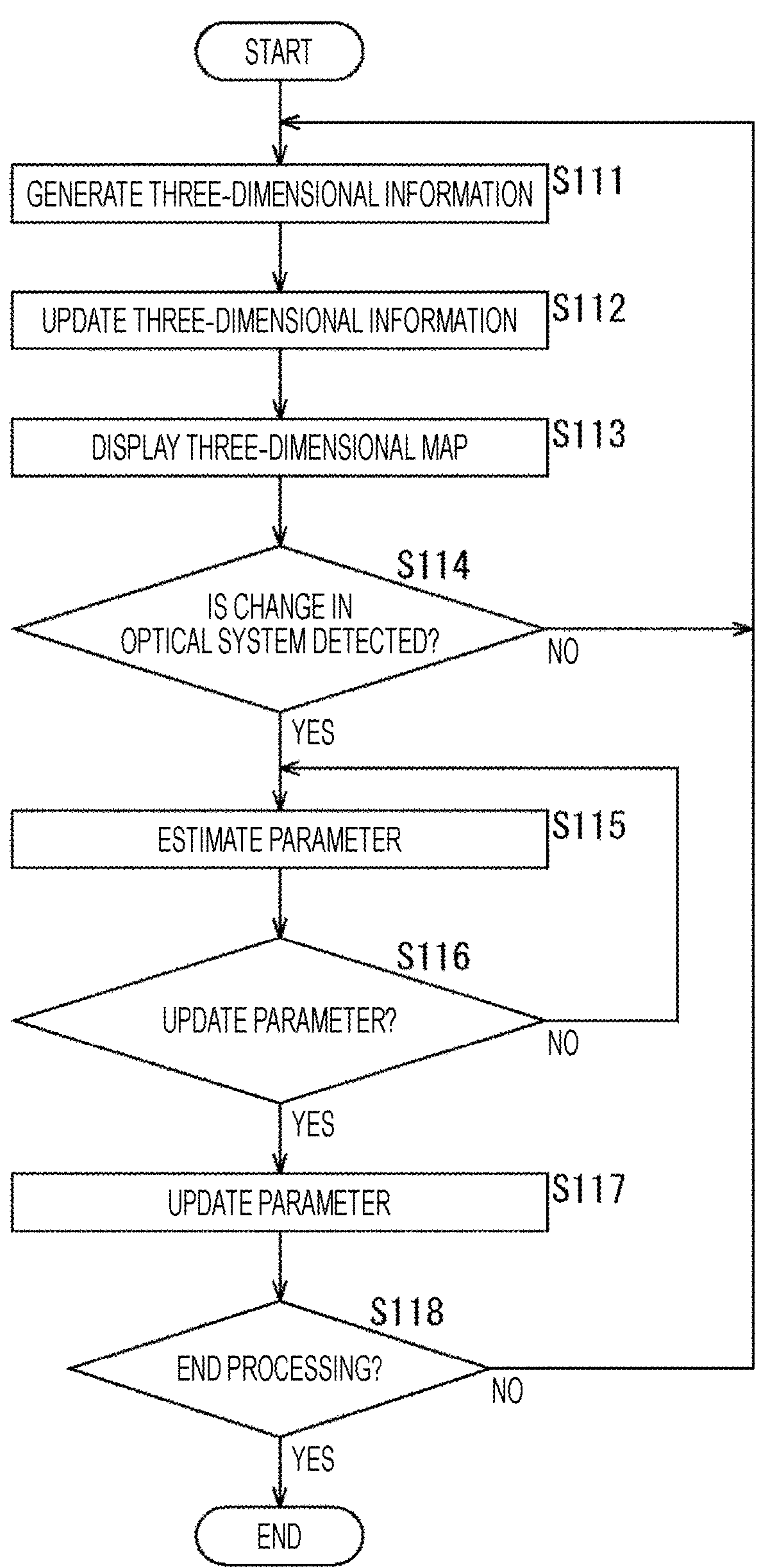
FIG. 4 is a flowchart illustrating three-dimensional information generation processing of the surgery assisting system in FIG. 2.

FIG. 4 is a flowchart illustrating three-dimensional information generation processing in the surgery assisting system 100.

In step S111, the three-dimensional information generation unit 113 generates three-dimensional information by using a parameter on the basis of the operative field image represented by the image signal obtained from the imaging unit 101.

In step S112, the three-dimensional information generation unit 113 updates the three-dimensional information generated so far by using the newly generated three-dimensional information.

In step S113, the display information generation unit 114 causes the display unit 103 to display the three-dimensional map on the basis of the three-dimensional information supplied from the three-dimensional information generation unit 113.

In step S114, the optical system change detection unit 111 determines whether or not a change in the optical system is detected.

In a case where it is determined in step S114 that a change in the optical system is detected, the parameter estimation unit 112 estimates a parameter in step S115. The generation of the three-dimensional information is stopped until the parameter is updated.

In step S116, the parameter estimation unit 112 determines whether or not to update the parameter serving as the generation condition of the three-dimensional information by using the estimated parameter. The determination here is performed on the basis of the reliability index of the parameter estimation result as described above.

In a case where it is determined in step S116 that the parameter is not updated, the processing returns to step S115, and the parameter estimation is repeated.

On the other hand, in a case where it is determined in step S116 that the parameter is updated, in step S117, the parameter estimation unit 112 updates the parameter serving as the generation condition of the three-dimensional information according to a new parameter.

The parameter updated by the parameter estimation unit 112 is supplied to the three-dimensional information generation unit 113.

In the three-dimensional information generation unit 113, for example, the generation of the three-dimensional information is continued by adjusting a scale of the three-dimensional map by using the new parameter so as to be compatible with the three-dimensional map before the change in the optical system is detected.

In step S118, the three-dimensional information generation unit 113 determines whether or not to end the three-dimensional information generation processing. In a case where it is determined in step S118 that the three-dimensional information generation processing is not ended, or in a case where it is determined in step S114 that a change in the optical system is not detected, the processing returns to step S111, and the processing in step S111 and subsequent steps is repeated.

On the other hand, in a case where it is determined in step S118 that the three-dimensional information generation processing is ended, the processing of the surgery assisting system 100 is ended.

In the above processing, in a case where a change occurs in the optical system of the imaging unit 101, the parameter serving as the generation condition of the three-dimensional information is updated, and the generation of the three-dimensional information is continued by using the updated parameter.

In order to generate accurate three-dimensional information in Visual-SLAM, it is necessary to set parameters including a focal length, an image center, and a distortion coefficient to appropriate values. In general Visual-SLAM, a parameter is obtained by camera calibration, and during operation (during surgery), the parameter obtained in advance is treated as a fixed value, and three-dimensional information is generated.

On the other hand, during surgery, an adjustment of the optical system such as zooming or replacement of the scope itself may be performed, therefore, the parameter is changed. Before and after the change in the optical system, a change occurs in a scale or the like of the generated three-dimensional information, or an error occurs. In order to use the changed three-dimensional information, the parameter is only required to be readjusted, but since it is necessary to detach the scope to manually perform camera calibration, it is not realistic to perform the camera calibration during surgery.

As described above, by continuing the generation of the three-dimensional information by using the updated parameter, even in a case where a change occurs in the optical system of the imaging unit 101 during surgery, accuracy of the three-dimensional information can be maintained without calibrating the parameter or the like again.

<Another Configuration Example of Surgery Assisting System (Example in which Robot Arm Holds Endoscope)>

Figure 5:
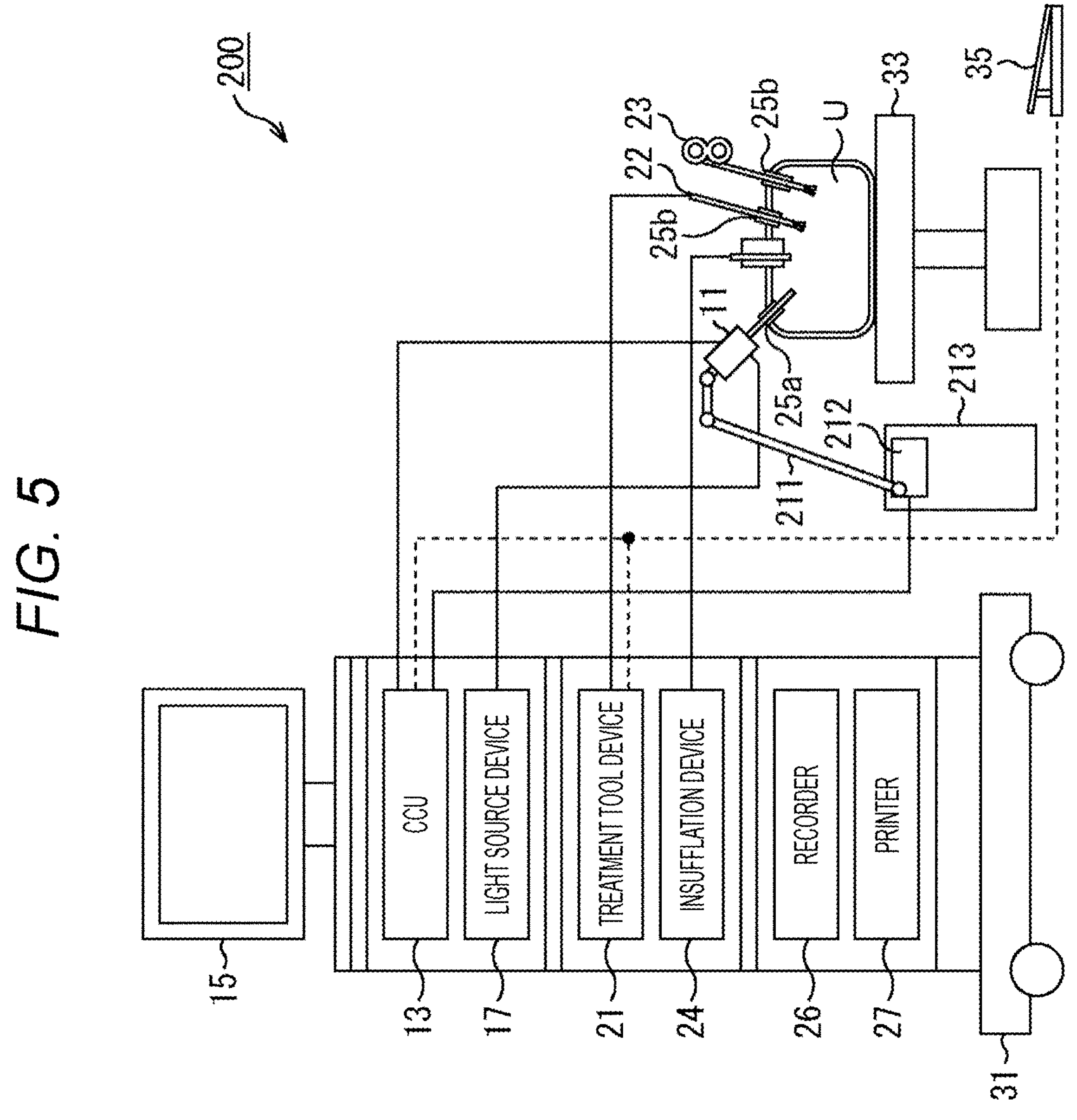
FIG. 5 is a diagram illustrating another configuration example of a surgery assisting system.

FIG. 5 is a diagram illustrating another configuration example of the surgery assisting system.

In the configuration illustrated in FIG. 5, a part corresponding to the configuration in FIG. 1 is denoted by the same reference numeral. Overlapping descriptions will be omitted appropriately. A configuration of a surgery assisting system 200 illustrated in FIG. 5 is different from the configuration illustrated in FIG. 1 in that a robot arm device 212 including a robot arm 211 and a cart 213 on which various devices for endoscopic surgery are mounted are provided.

The robot arm device 212 holds the endoscope 11 with the robot arm 211. A position and orientation information of the endoscope 11, which is acquired by the robot arm device 212, is supplied to the CCU 13 (information processing unit 102 in FIG. 2).

In a case where the endoscope 11 is held by the robot arm 211, the position and orientation information of the endoscope 11, which is supplied from the robot arm device 212, is used for detecting a change in the optical system and estimating a parameter.

<Functional Configuration Example of Surgery Assisting System>

A functional configuration of the surgery assisting system 200 in FIG. 5 is the same as the configuration described with reference to FIG. 2. With reference to FIG. 2 again, a method of detecting a change in an optical system, the method using position and orientation information of the imaging unit 101 (endoscope 11) and a method of estimating a parameter will be described for the surgery assisting system 200.

The position and orientation information of the imaging unit 101, which is supplied from the robot arm device 212, is input to the optical system change detection unit 111 and the three-dimensional information generation unit 113.

Optical System Change Detection Unit 111

The optical system change detection unit 111 detects a change in the optical system on the basis of a locus of a self-position of the imaging unit 101, which is supplied from the robot arm device 212.

According to SLAM, the self-position of the imaging unit 101, which is estimated by the three-dimensional information generation unit 113, causes an error when the optical system is changed in a similar manner to the three-dimensional map. The optical system change detection unit 111 compares an actual locus of the self-position of the imaging unit 101, which is obtained from the robot arm device 212, with a locus of a self-position, which is estimated by the three-dimensional information generation unit 113, and detects that a change in the optical system occurs in a case where the errors of the loci are large.

Furthermore, in general, in a case where an angle of view is changed, it is difficult to distinguish zooming in and out from a movement of the imaging unit 101 in an optical axis direction. However, in a case where the imaging unit 101 is held by the robot arm 211, presence or absence of a movement of the imaging unit 101 can be detected. Therefore, it is possible to detect a change in the optical system by using the angle of view. That is, even in a case where a change occurs in the angle of view of the operative field image, when the imaging unit 101 is not moved, it is detected that there is a change in the optical system.

Note that, even in a case where the imaging unit 101 is held by the scopist, when the presence or absence of the movement of the imaging unit 101 can be detected by a sensor or the like, the change in the optical system may be detected by using the change in the angle of view and the presence or absence of the movement of the imaging unit 101, in a similar manner to the case of the robot arm 211.

As a method of detecting a change in the optical system, for example, there is a method of detecting a change by recording feature points between frames and tracking a change of the feature points close to an outer peripheral side of the operative field image.

Parameter Estimation Unit 112

The parameter estimation unit 112 estimates a parameter by using the position and orientation information of the imaging unit 101, which is obtained from the robot arm device 212. Estimation of a parameter based on information obtained from a robot arm is disclosed in, for example, "Radu Horaud, "The Advantage of Mounting a Camera onto a Robot Arm", Europe-China Workshop on Geometrical Modelling and Invariants for Computer Vision, 1995, pp 206-213.".

An operation of the surgery assisting system 200 in FIG. 5 is basically the same as the operation described with reference to FIG. 4.

As described above, according to the first embodiment, even in a case where the optical system is changed during surgery, the accuracy of the three-dimensional information after the change can be maintained, and the three-dimensional information generated before the change and the three-dimensional information generated after the change can be continuously used.

2. Second Embodiment (Use in Training)

<Configuration Example of Surgery Assisting System>

FIG. 6 is a block diagram illustrating an example of a hardware configuration of an information processing device 300 configuring a surgery assisting system according to the second embodiment of the present technology.

A surgery assisting system including the information processing device 300 of FIG. 6 is, for example, a system that displays an image during surgery or the like, which is recorded in the surgery assisting system of FIG. 1, after the surgery, the surgery assisting system being used for training of an operator or a student. The surgery assisting system including the information processing device 300 can also be referred to as an endoscopic surgery training system.

As illustrated in FIG. 6, the information processing device 300 includes, for example, a computer or the like.

A CPU 301, a ROM 302, and a RAM 303 are connected to each other by a bus 304.

An input and output interface 305 is connected to the bus 304 as well. An input unit 306 including a keyboard, a mouse, and the like, and an output unit 307 including a display, a speaker, and the like are connected to the input and output interface 305.

Furthermore, a storage unit 308 including a hard disk, a nonvolatile memory, and the like, a communication unit 309 including a network interface and the like, and a drive 310 that drives a removable medium 311 are connected to the input and output interface 305.

The second embodiment is different from the first embodiment in that it is not necessary to immediately estimate a parameter in a case where the surgery assisting system is used for training. It is possible to perform processing after the entire operative field image is read once.

In the second embodiment, a three-dimensional map (integrated three-dimensional map) optimized for the entire recorded image is generated once, and then the SLAM including estimation of a camera orientation is operated to display the three-dimensional map.

<Functional Configuration Example of Surgery Assisting System>

(Overall Configuration)

Figure 7:
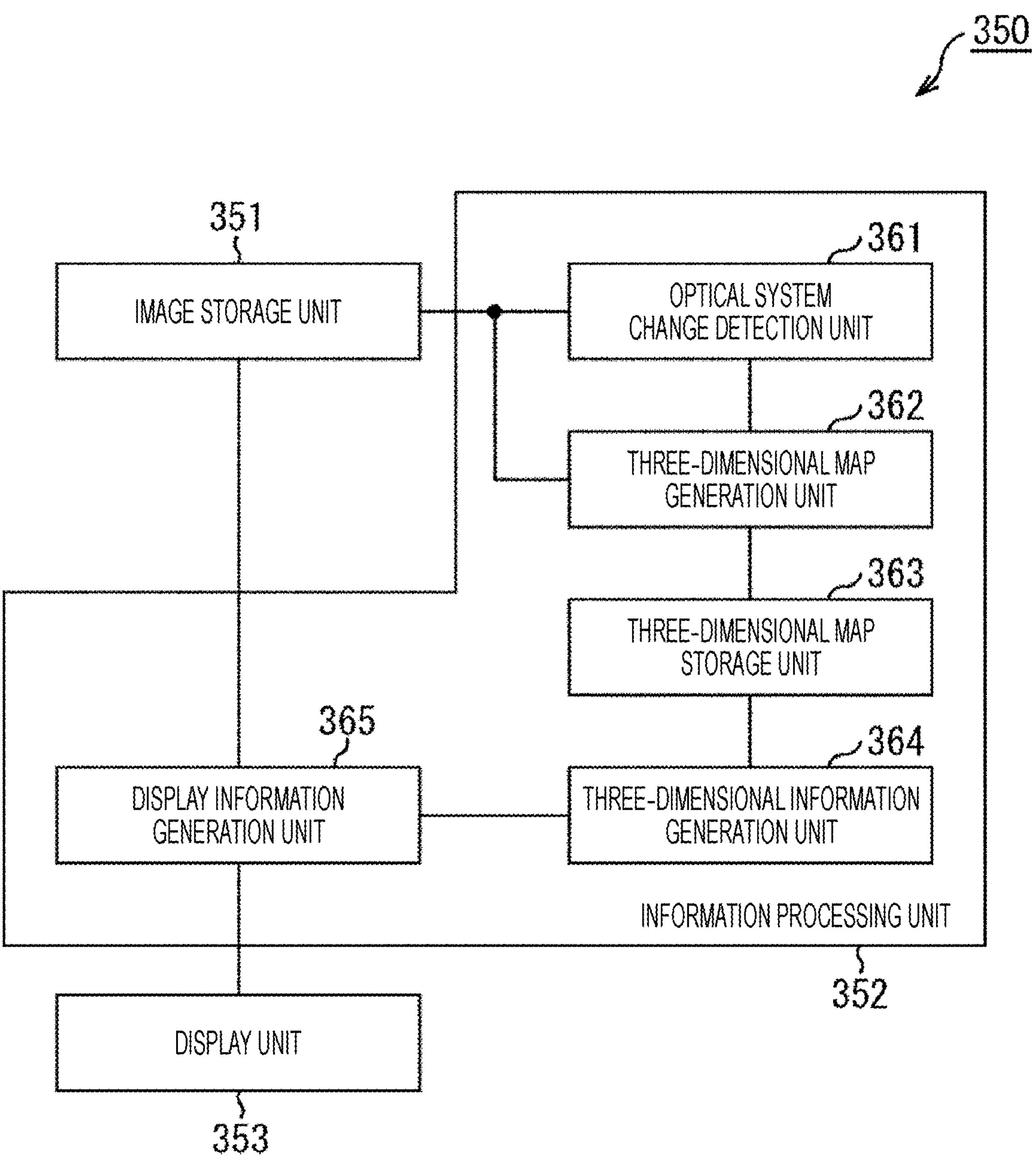
FIG. 7 is a block diagram illustrating a functional configuration example of a surgery assisting system according to a second embodiment of the present technology.

FIG. 7 is a block diagram illustrating a functional configuration example of the surgery assisting system. A surgery assisting system 350 in FIG. 7 includes an image storage unit 351, an information processing unit 352, and a display unit 353.

The image storage unit 351 corresponds to the storage unit 308 in FIG. 6. The image storage unit 351 stores an operative field image captured by the endoscope 11 (FIG. 1) during surgery.

The information processing unit 352 is implemented by the CPU 301 of FIG. 6. The information processing unit 352 performs signal processing on the operative field image stored in the image storage unit 351, and supplies the operative field image obtained by performing the signal processing to the display unit 353.

The display unit 353 corresponds to a display configuring the output unit 307 of FIG. 6. The display unit 353 displays the operative field image on the basis of the image signal supplied from the information processing unit 352.

(Detailed Configuration of Information Processing Unit 352)

The information processing unit 352 includes an optical system change detection unit 361, a three-dimensional map generation unit 362, a three-dimensional map storage unit 363, a three-dimensional information generation unit 364, and a display information generation unit 365. At least a part of the information processing unit 352 is implemented by the CPU 301 executing a predetermined program of FIG. 6. Descriptions overlapping with the above description will be appropriately omitted.

Optical System Change Detection Unit 361

The optical system change detection unit 361 detects a change in the optical system with reference to the entire operative field image stored in the image storage unit 351. The detection of the change in the optical system is performed in a similar manner to the optical system change detection unit 111 of FIG. 2.

The optical system change detection unit 361 sets, as a section, a segment of a frame having the same parameter, that is, a segment of a frame without a change in the optical system.

The optical system change detection unit 361 estimates a parameter of each section. The estimation of a parameter is performed in a similar manner to the parameter estimation unit 112 in FIG. 2. The optical system change detection unit 361 outputs the parameter of each section to the three-dimensional map generation unit 362.

Three-Dimensional Map Generation Unit 362

The three-dimensional map generation unit 362 generates a three-dimensional map of each section by using the parameter supplied from the optical system change detection unit 361. The three-dimensional map generated by the three-dimensional map generation unit 362 is a three-dimensional map of a subject appearing in the operative field images of a plurality of frames configuring the section.

In the generation of the three-dimensional map, for example, Multiview stereo or SfM, which are capable of generating the three-dimensional map from a plurality of viewpoints, can be used in addition to Visual SLAM or RGB-D-SLAM. Multiview stereo is described in, for example, "Multi-View Stereo: A Tutorial. Foundations and. TrendsR in Computer Graphics and Vision, vol. 9, no. 1-2, 2013, pp. 1-148." and "Evaluation of multi-view 3D reconstruction software, CAIP 2015: Computer Analysis of Images and Patterns, pp. 450-461.".

The three-dimensional map generation unit 362 outputs the three-dimensional map of each section to the three-dimensional map storage unit 363.

Three-Dimensional Map Storage Unit 363

The three-dimensional map storage unit 363 stores the three-dimensional map of each section, which is generated by the three-dimensional map generation unit 362.

Three-Dimensional Information Generation Unit 364

The three-dimensional information generation unit 364 integrates the three-dimensional maps of each section, which are stored in the three-dimensional map storage unit 363, and generates a three-dimensional map integrated through all the sections.

Since the three-dimensional map generated in each section has a different parameter for each section, a scale and a position are different, and it is difficult to integrate the three-dimensional maps as they are, and use the integrated three-dimensional maps for SLAM processing. Therefore, in the three-dimensional information generation unit 364, a scale and a positional relationship of each section are corrected, and the three-dimensional map is integrated while optimizing the scale, and the like.

Specifically, the three-dimensional information generation unit 364 estimates a scale of the three-dimensional map of the other section with respect to the three-dimensional map serving as a reference in the sections, so that scales of the three-dimensional maps in all the sections are integrated.

Each of the points of the three-dimensional map generated in each section holds a vector which is referred to as a feature amount and represents a feature of the point. The three-dimensional information generation unit 364 can identify a portion overlapped in the three-dimensional map by searching for points holding the same feature amount in different three-dimensional maps. In the overlapped portion, the three-dimensional information generation unit 364 identifies a scale and a positional relationship, in which residual is minimized, by using the least squares method.

Note that, the point holding the feature amount includes a feature point of the operative field image, a feature point of the three-dimensional map, or the like.

The feature points of the operative field image are, for example, SIFT, SURF, ORB, AKAZE, and the like.

The feature points of the three-dimensional map are, for example, SHOT, PFH, PPF, and the like.

Furthermore, in a case where each point of the generated three-dimensional map does not hold the feature amount, and identification of corresponding points, that is, identification of overlapped portions cannot be performed in the three-dimensional maps, ICP that can perform registration of two point groups can also be used while simultaneously estimating the correspondence relationship.

The three-dimensional information generation unit 364 generates three-dimensional information according to SLAM including estimation of a self-position and orientation of the camera by using the integrated three-dimensional map.

The three-dimensional information generation unit 364 outputs the generated three-dimensional information to the display information generation unit 365.

In the above description, an example of a case where the three-dimensional map of each section is generated in the three-dimensional map generation unit 362 has been described, but three-dimensional information (position and orientation information, and three-dimensional map) of each section may be generated in the three-dimensional map generation unit 362. The three-dimensional information of each section is stored in the three-dimensional map storage unit 363.

At this time, in the three-dimensional information generation unit 364, pieces of three-dimensional information of each section are integrated, the SLAM processing including estimation of the self-position and orientation of the camera is performed by using the integrated three-dimensional information, and the three-dimensional information is generated again.

Display Information Generation Unit 365

The display information generation unit 365 causes the display unit 353 to display the operative field image on the basis of the image signal read from the image storage unit 351 in a similar manner to the display information generation unit 114 of FIG. 2.

Furthermore, the display information generation unit 365 causes the display unit 353 to display the integrated three-dimensional map on the basis of the three-dimensional information supplied from the three-dimensional information generation unit 364.

<Operation Example of Surgery Assisting System>

Figure 8:
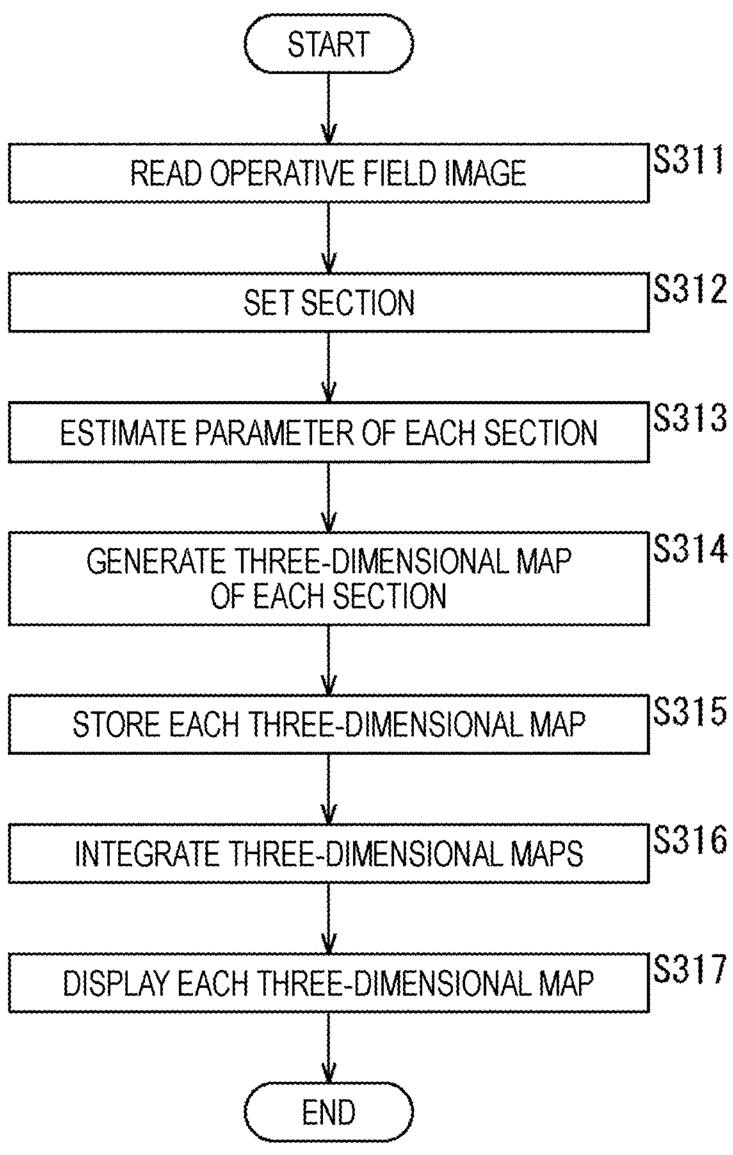
FIG. 8 is a flowchart illustrating three-dimensional information generation processing of the surgery assisting system in FIG. 7.

FIG. 8 is a flowchart illustrating three-dimensional information generation processing in the surgery assisting system 350.

In step S311, the optical system change detection unit 361 reads the operative field image represented by the image signal obtained from the image storage unit 351.

In step S312, the optical system change detection unit 361 refers to the entire operative field image, and sets, as a section, a segment of a frame having the same parameter, that is, a segment of a frame without a change in the optical system on the basis of the detection result of the change in the optical system.

In step S313, the optical system change detection unit 361 estimates a parameter of each section.

In step S314, the three-dimensional map generation unit 362 generates a three-dimensional map of each section.

In step S315, the three-dimensional map storage unit 363 stores the three-dimensional map of each section, which is generated by the three-dimensional map generation unit 362.

In step S316, the three-dimensional information generation unit 364 integrates the three-dimensional maps of each section, which is stored in the three-dimensional map storage unit 363, and generates the integrated three-dimensional map. The three-dimensional information generation unit 364 generates three-dimensional information according to SLAM including estimation of a self-position and orientation of the camera by using the integrated three-dimensional map.

In step S317, the display information generation unit 365 causes the display unit 353 to display the three-dimensional map on the basis of the three-dimensional information supplied from the three-dimensional information generation unit 364.

In a case where the three-dimensional map is displayed on the display unit 353 in step S317, processing of the surgery assisting system 350 is ended.

In the above processing, the parameter serving as the generation condition of the three-dimensional information is updated for each section set according to the change in the optical system of the imaging unit 101, and the three-dimensional maps generated for each section are integrated.

As described above, according to the second embodiment, in a case where the surgery assisting system is used for training after surgery or the like, it is possible to prevent an error from occurring in the three-dimensional information even when a change in the optical system occurs during surgery.

3. Application Example

Next, an example of a case where a surgical video microscope device including an arm is used as an application example of the surgery assisting system according to the embodiment of the present technology will be described with reference to FIG. 9.

Figure 9:
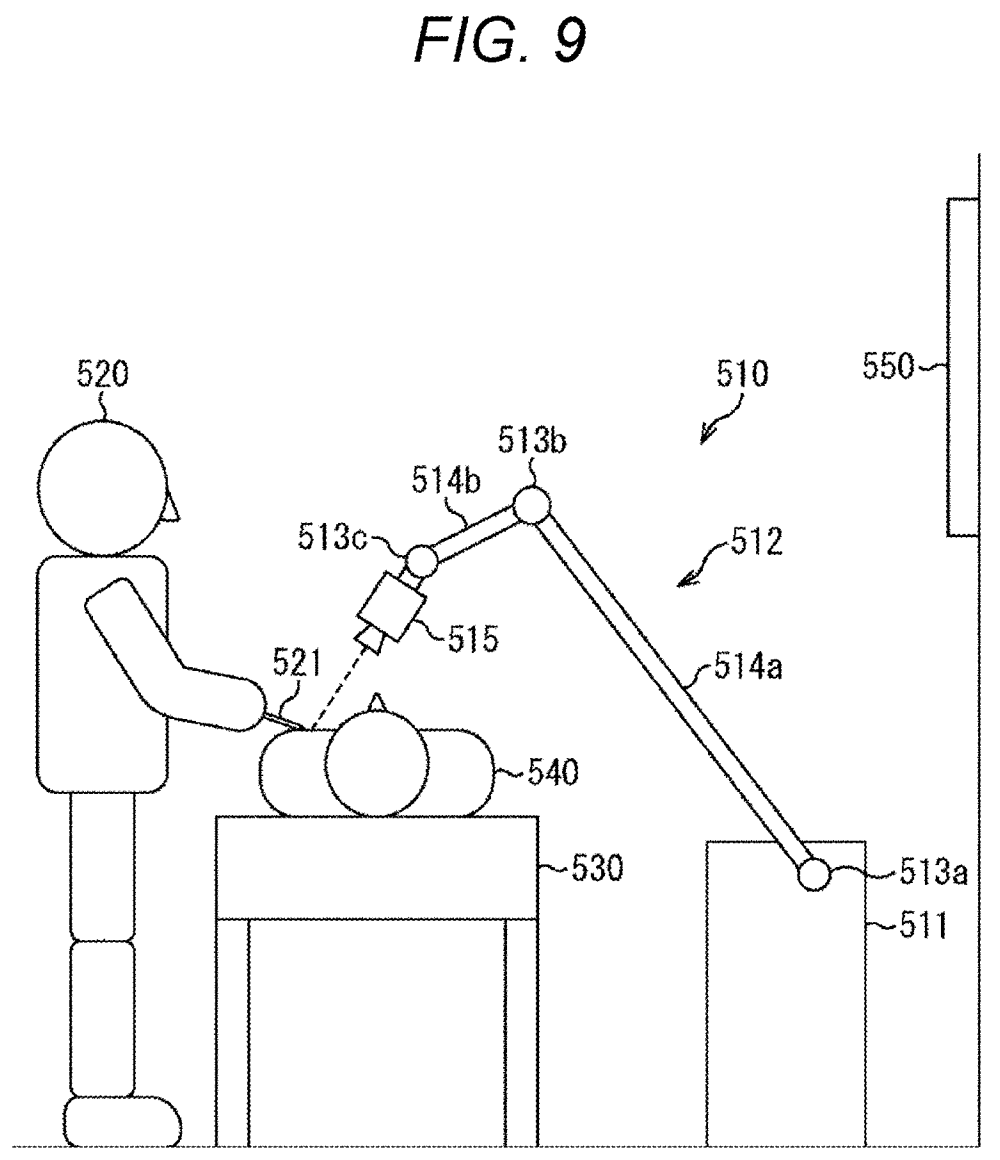

FIG. 9 illustrates an example of a microscopic surgery system using the surgical video microscope device as an observation medical device for observing an inside of a patient's body.

FIG. 9 illustrates a state in which a medical doctor who is an operator (user) 520 is performing surgery on an operation target (patient) 540 on an operation table 530 by using, for example, a surgical instrument 521 such as a scalpel, tweezers, or forceps.

Note that, in the following description, the operation is a generic term for various medical treatments such as surgery and an examination, which is performed on the patient who is the operation target 540 by a medical doctor who is the user 520. Furthermore, in the example of FIG. 9, a state of the surgery is illustrated as an example of the operation, but the operation using a surgical video microscope device 510 is not limited to surgery, and may be other various operations.

The surgical video microscope device 510 according to the embodiment of the present technology is provided beside the operation table 530.

The surgical video microscope device 510 includes a base unit 511 which is a base, an arm unit 512 extending from the base unit 511, and an imaging unit 515 connected to a distal end of the arm unit 512 as a distal end unit.

The arm unit 512 includes a plurality of joints 513*a*, 513*b*, and 513*c*, a plurality of links 514*a* and 514*b* connected by the joints 513*a* and 513*b*, and the imaging unit 515 provided at the distal end of the arm unit 512.

In the example of FIG. 9, for simplicity, the arm unit 512 includes three joints 513*a* to 513*c*, and two links 514*a* and 514*b*. Actually, in consideration of a degree of freedom of the position and orientation of the arm unit 512 and the imaging unit 515, the number and shapes of the joints 513*a* to 513*c* and the links 514*a* and 514*b*, directions of drive shafts of the joints 513*a* to 513*c*, and the like may be appropriately set so as to realize a desired degree of freedom.

The joints 513*a* to 513*c* have a function of rotatably connecting the links 514*a* and 514*b* to each other, and a driving of the arm unit 512 is controlled by driving a rotation of the joints 513*a* to 513*c*.

The imaging unit 515 is connected to the distal end of the arm unit 512 as a distal end unit.

The imaging unit 515 is a unit that acquires an image to be captured by including an optical system that acquires an optical image of a subject, and is constituted as, for example, a camera or the like capable of capturing a moving image or a still image. As illustrated in FIG. 9, the self-position and orientation of the arm unit 512 and the imaging unit 515 is controlled by the surgical video microscope device 510 so that the imaging unit 515 provided at the distal end of the arm unit 512 images the state of the operation site of an operation target 540.

Note that, the configuration of the imaging unit 515 connected to the distal end of the arm unit 512 as a distal end unit is not particularly limited, and for example, the imaging unit 515 may be constituted as an endoscope or a microscope. Furthermore, the imaging unit 515 may be constituted to be detachable from the arm unit 512.

With such a configuration, for example, the imaging unit 515 corresponding to a use application may be appropriately connected to the distal end of the arm unit 512 as a distal end unit. Note that, here, a description will be given focusing on a case where the imaging unit 515 is applied as a distal end unit, but it goes without saying that the distal end unit connected to the distal end of the arm unit 512 is not necessarily limited to the imaging unit 515.

Furthermore, a display device 550 such as a monitor or a display is installed at a position facing the user 520. The image of the operation site, which is acquired by the imaging unit 515, is subjected to various image processing by an image processing device built in or externally attached to the surgical video microscope device 510, for example, and then is displayed, as an electronic image, on a display screen of the display device 550.

With such a configuration, the user 520 can perform various treatments (for example, surgery and the like) while observing the electronic image of the operation site, which is displayed on the display screen of the display device 550.

Here, in the example of FIG. 9, the imaging unit 515 includes, for example, the imaging unit 101 described with reference to FIG. 2. Furthermore, the image processing device that performs various image processing on the image of the operation site, which is acquired by the imaging unit 515, corresponds to an example of the information processing unit 102 described with reference to FIG. 2. In a similar manner, the display device 550 corresponds to an example of the display unit 103 described with reference to FIG. 2.

Furthermore, in the example of FIG. 9, the arm unit 512 corresponds to an example of the robot arm 211 described with reference to FIG. 5. In a similar manner, the surgical video microscope device 510 includes the robot arm device 212 described with reference to FIG. 5.

4. Hardware Configuration

Next, an example of a hardware configuration of the information processing device configuring the surgery assisting system according to the embodiment of the present technology will be described in detail with reference to FIG. 10.

FIG. 10 is a block diagram illustrating an example of a hardware configuration of an information processing device 900 configuring a surgery assisting system according to the embodiment of the present technology.

As illustrated in FIG. 10, the information processing device 900 includes a CPU 901, a ROM 903, and a RAM 905. Moreover, the information processing device 900 includes a host bus 907, a bridge 909, an external bus 911, an interface 913, an input device 915, an output device 917, and a storage device 919. Note that, the information processing device 900 may include a drive 921, a connection port 923, and a communication device 925.

The CPU 901 functions as an arithmetic processing device and a control device, and controls the overall operation or a part of the operation in the information processing device 900 according to various programs recorded in the ROM 903, the RAM 905, the storage device 919, or a removable recording medium 927.

The ROM 903 stores a program used by the CPU 901, an operation parameter, and the like. The RAM 905 primarily stores a program used by the CPU 901, a parameter that is appropriately changed in execution of the program, and the like. These are mutually connected by the host bus 907 including an internal bus such as a CPU bus. Note that, each configuration of the information processing unit 102 described with reference to FIG. 2 is implemented by, for example, the CPU 901.

The host bus 907 is connected to the external bus 911 such as a peripheral component interconnect/interface (PCI) bus via the bridge 909. The input device 915, the output device 917, the storage device 919, the drive 921, the connection port 923, and the communication device 925 are connected to the external bus 911 via the interface 913.

For example, the input device 915 is operation means operated by the user, such as a mouse, a keyboard, a touch panel, a button, a switch, a lever, and a pedal. Furthermore, the input device 915 may be, for example, remote control means (so-called remote controller) using infrared ray or other radio wave. The input device 915 may be, for example, an external connection device 929 such as a mobile phone, a smartphone, or a tablet terminal, which correspond to the operation of the information processing device 900.

The input device 915 includes, for example, an input control circuit that generates an input signal on the basis of information input by the user using the above-described operation means and outputs the input signal to the CPU 901.

By operating the input device 915, the user can input various data to the information processing device 900 and instruct the information processing device 900 to perform a processing operation.

The output device 917 includes a device capable of visually or aurally notifying the user of the acquired information. Specifically, examples of the output device 917 include a display device such as a CRT display device, a liquid crystal display device, a plasma display device, an EL display device, and a lamp, an audio output device such as a speaker and a headphone, a printer, and the like.

The output device 917 outputs, for example, a result obtained by various processing performed by the information processing device 900. Specifically, the display device displays, as a text or an image, a result obtained by various processing performed by the information processing device 900. On the other hand, the audio output device converts an audio signal including reproduced audio data, acoustic data, or the like into an analog signal, and outputs the analog signal. Note that, the display unit 103 described with reference to FIG. 2 is implemented by, for example, the output device 917.

The storage device 919 is a data storage device constituted as an example of a storage unit of the information processing device 900. The storage device 919 includes, for example, a magnetic storage unit device such as a hard disk drive (HDD), a semiconductor storage device, an optical storage device, a magneto-optical storage device, and the like. The storage device 919 stores a program executed by the CPU 901, various data, and the like.

The drive 921 is a recording-medium reader/writer, and is built in or externally attached to the information processing device 900. The drive 921 reads information recorded on the mounted removable recording medium 927 such as a magnetic disk, an optical disk, a magneto-optical disk, or a semiconductor memory, and outputs the information to the RAM 905. Furthermore, the drive 921 can also write a record on the mounted removable recording medium 927 such as a magnetic disk, an optical disk, a magneto-optical disk, or a semiconductor memory.

The removable recording medium 927 is, for example, a DVD medium, an HD-DVD medium, a Blu-ray (registered trademark) medium, or the like. Furthermore, the removable recording medium 927 may be CompactFlash (CF) (registered trademark), a flash memory, a secure digital (SD) memory card, or the like. Moreover, the removable recording medium 927 may be, for example, an integrated circuit (IC) card on which a non-contact IC chip is mounted, an electronic device, or the like.

The connection port 923 is a port for directly connecting the external connection device 929 to the information processing device 900. Examples of the connection port 923 include a universal serial bus (USB) port, an IEEE 1394 port, a small computer system interface (SCSI) port, and the like. Other examples of the connection port 923 include an RS-232C port, an optical audio terminal, a high-definition multimedia interface (HDMI) (registered trademark) port, and the like. By connecting the external connection device 929 to the connection port 923, the information processing device 900 directly acquires various data from the external connection device 929 or provides various data to the external connection device 929.

The communication device 925 is, for example, a communication interface including a communication device or the like for connecting to a communication network (network) 931. The communication device 925 is, for example, a communication card or the like for a wired or wireless local area network (LAN), Bluetooth (registered trademark), or a wireless USB (WUSB). Furthermore, the communication device 925 may be a router for optical communication, a router for asymmetric digital subscriber line (ADSL), a modem for various types of communication, or the like.

For example, the communication device 925 can transmit and receive a signal to and from the Internet and other communication devices according to a predetermined protocol such as TCP/IP. Furthermore, the communication network 931 connected to the communication device 925 may include a network or the like connected in a wired or wireless manner. The communication network 931 may be, for example, the Internet, a home LAN, or a communication network in which infrared ray communication, radio wave communication, or satellite communication is performed.

Each constituent element of the information processing device 300 of FIG. 5 and the information processing device 900 of FIG. 10, which are described above, may be constituted by using a general purpose member, or may be constituted of hardware specialized for a function of each constituent element. Therefore, it is possible to appropriately change the hardware configuration to be used according to the technology level at the time of carrying out the embodiment of the present technology.

Moreover, a computer program for implementing each function of the information processing device 300 and the information processing device 900, which constitute the surgery assisting system according to the embodiment of the present technology, can be produced, and mounted on a personal computer or the like. Furthermore, it is also possible to provide a computer-readable recording medium storing such a computer program. The recording medium is, for example, a magnetic disk, an optical disk, a magneto-optical disk, a flash memory, or the like. Furthermore, the computer program may be distributed via, for example, a network without using the recording medium.

Note that, the program executed by the computer may be a program by which processing is performed in time series in order described in the present specification, or may be a program by which processing is performed in parallel or at a necessary timing when a call is made.

5. Others

As described above, in the present technology, operative field data acquired by the medical observation device is acquired, and a change in the optical system of the medical observation device is detected. Then, in a case where a change in the optical system is detected, a parameter determined depending on the optical system after the change is estimated, and a generation condition of three-dimensional information based on the operative field data is set by using the estimation result. Therefore, even in a case where a change occurs in the optical system, the accuracy of the three-dimensional information can be maintained.

Even in a case where a change occurs in the optical system during surgery, the accuracy of the three-dimensional information can be maintained without calibrating the parameter again.

Furthermore, in a case where the surgery assisting system is used for training after surgery or the like, it is possible to prevent an error from occurring in the three-dimensional information even when a change in the optical system occurs in the operative field image.

Note that, in the present specification, a system means a set of a plurality of constituent elements (devices, modules (parts), and the like), and it does not matter whether or not all the constituent elements are in the same housing. Therefore, a plurality of devices housed in separate housings and connected via a network and one device in which a plurality of modules is housed in one housing are both systems.

Furthermore, the effects described in the present specification are merely examples and are not limited, and other effects may be provided.

An embodiment of the present technology is not limited to the above-described embodiments, and various modifications can be made without departing from the gist of the present technology.

For example, the present technology can have a cloud computing configuration in which one function is shared and processing is performed in cooperation by a plurality of devices via a network.

Furthermore, each step described in the above-described flowchart can be executed by one device or can be shared and executed by a plurality of devices.

Moreover, in a case where a plurality of processing is included in one step, the plurality of processing included in one step can be executed by one device or can be shared and executed by a plurality of devices.

<Combination Example of Configuration>

The present technology can also have the following configurations.

(1)

A medical observation system including:

an acquisition unit configured to acquire operative field data acquired by a medical observation device;

a detection unit configured to detect a change in an optical system of the medical observation device;

an estimation unit configured to estimate a parameter determined depending on the optical system after a change occurs in the optical system in a case where the change in the optical system is detected by the detection unit; and a setting unit configured to set a generation condition of three-dimensional information based on the operative field data by using an estimation result of the estimation unit.

(2)

The medical observation system according to (1), in which the detection unit detects a change in the optical system by detecting a change in an operative field image represented by the operative field data.

(3)

The medical observation system according to (1), in which the detection unit detects a change in the optical system by detecting a change of a focal length of an operative field image represented by the operative field data.

(4)

The medical observation system according to (1), in which the detection unit detects a change in the optical system by using a locus of a position of the medical observation device held by a robot arm.

(5)

The medical observation system according to (1), in which the detection unit detects that there is a change in the optical system in a case where a change occurs in an angle of view of an operative field image represented by the operative field data and the medical observation device held by a robot arm is not moved.

(6)

The medical observation system according to any one of (1) to (5), in which the detection unit divides the operative field data for each section that is a segment including frames of a plurality of operative field images on the basis of the change in the optical system, and the estimation unit estimates the parameter for each section.

(7)

The medical observation system according to any one of (1) to (5), in which the estimation unit estimates the parameter corresponding to information of the optical system, which is acquired from the medical observation device, on the basis of a table which is obtained in advance and represents a relationship between the information of the optical system and the parameter.

(8)

The medical observation system according to any one of (1) to (5), in which the estimation unit estimates the parameter on the basis of the operative field data.

(9)

The medical observation system according to (8), in which the estimation unit estimates the parameter from an operative field image represented by the operative field data and generates a reliability index of a matrix of the parameter.

(10)

The medical observation system according to any one of (1) to (9), further including a three-dimensional information generation unit configured to generate the three-dimensional information by using the parameter estimated by the estimation unit.

(11)

The medical observation system according to (10), in which the three-dimensional information generation unit stops generating the three-dimensional information in a case where a change in the optical system is detected by the detection unit, and resumes generating the three-dimensional information by using the estimated parameter in a case where the parameter is estimated by the estimation unit.

(12)

The medical observation system according to any one of (1) to (11), further including a display control unit configured to control a display of an operative field image represented by the operative field data or the three-dimensional information.

(13)

The medical observation system according to (12), in which the display control unit displays a detection result of a change in the optical system, which is obtained by the detection unit.

(14)

The medical observation system according to (13), in which the display control unit displays, as the detection result, information representing that a scope of the medical observation device is replaced.

(15)

The medical observation system according to (13), in which the display control unit displays, as the detection result, information related to a scope of the medical observation device.

(16)

The medical observation system according to (13), in which the display control unit displays the three-dimensional information before a change and the three-dimensional information after a change.

(17)

A medical observation method including causing a medical observation system to:

acquire operative field data acquired by a medical observation device;

detect a change in an optical system of the medical observation device;

estimate a parameter determined depending on the optical system after a change occurs in the optical system in a case where the change in the optical system is detected; and set a generation condition of three-dimensional information based on the operative field data by using an estimation result.

(18)

A medical observation device including:

an imaging unit configured to image an operative field and generate operative field data; and an output unit configured to output the operative field data, the medical observation device being used in a medical observation system in which a change in an optical system of the imaging unit is detected, in a case where a change in the optical system is detected, a parameter determined depending on the optical system after the change is estimated, and a generation condition of three-dimensional information based on the operative field data is set by using an estimation result.

REFERENCE SIGNS LIST

1 Surgery assisting system
11 Endoscope
13 CCU
15 Display device
100 Surgery assisting system
101 Camera
102 Information processing unit
103 Display unit
111 Optical system change detection unit
112 Parameter estimation unit
113 Three-dimensional information generation unit
114 Display information generation unit
200 Surgery assisting system
211 Robot arm
212 Robot arm device
300 Surgery assisting system
301 CPU
307 Output unit
308 Storage unit
350 Surgery assisting system
351 Image storage unit
352 Information processing unit
353 Display unit
361 Optical system change detection unit

362 Three-dimensional map generation unit
363 Three-dimensional map storage unit
364 Three-dimensional information generation unit
365 Display information generation unit

The invention claimed is:

1. A medical observation system comprising:
circuitry configured to:
acquire medical field data acquired by a medical observation device;
detect a change in an optical system of the medical observation device;
determine a parameter based on information indicating a type of a scope of the medical observation after the change occurs in the optical system; and
set a generation condition of three-dimensional information based on the medical field data by using the determined parameter.

2. The medical observation system according to claim 1, wherein the circuitry is configured to integrate first three-dimensional information generated before the change in the optical system with second three-dimensional information generated after the change by optimizing a scale of the second three-dimensional information to be compatible with the first three-dimensional information using the determined parameter.

3. The medical observation system according to claim 1, wherein the circuitry is configured to estimate the parameter using self-calibration of a medical field image, generate a reliability index for the estimated parameter, and automatically update the generation condition only if the reliability index exceeds a preset threshold.

4. The medical observation system according to claim 1, wherein the circuitry is configured to detect a change in the optical system by using a locus of a position of the medical observation device held by a robot arm.

5. The medical observation system according to claim 1, wherein the circuitry is configured to detect the change in the optical system by comparing an actual locus of a position of the medical observation device obtained from a robot arm with an estimated locus derived from three-dimensional information generated from the medical field data.

6. The medical observation system according to claim 1, wherein the circuitry is configured to: divide the medical field data for each section that is a segment including frames of a plurality of medical field images on a basis of the change in the optical system, and determine the parameter for each section.

7. The medical observation system according to claim 1, wherein the circuitry is configured to determine the parameter corresponding to information of the optical system, which is acquired from the medical observation device, based on a table which is obtained in advance and represents a relationship between the information of the optical system and the parameter.

8. The medical observation system according to claim 1, wherein the circuitry is configured to detect the change in the optical system in response to a change in an angle of view of a medical field image represented by the medical field data and the medical observation device is not moved.

9. The medical observation system according to claim 8, wherein the circuitry is configured to determine the parameter from a medical field image represented by the medical field data and generates a reliability index of a matrix of the parameter.

10. The medical observation system according to claim 1, wherein the circuitry is configured to generate the three-dimensional information by using the parameter determined.

11. The medical observation system according to claim 10, wherein the circuitry is configured to: stop generating the three-dimensional information in a case where a change in the optical system is detected, and resume generating the three-dimensional information by using the determined parameter in a case where the parameter is determined.

12. The medical observation system according to claim 1, further comprising the circuitry is configured to control a display of a medical field image represented by the medical field data or the three-dimensional information.

13. The medical observation system according to claim 12, wherein the circuitry is configured to output a detection result of a change in the optical system.

14. The medical observation system according to claim 13, wherein the circuitry is configured to output, as the detection result, information representing that a scope of the medical observation device is replaced.

15. The medical observation system according to claim 13, wherein the circuitry is configured to output, as the detection result, information related to a scope of the medical observation device.

16. The medical observation system according to claim 13, wherein the circuitry is configured to output the three-dimensional information before a change and the three-dimensional information after a change.

17. A medical observation method comprising causing a medical observation system to:
acquire medical field data acquired by a medical observation device;
detect a change in an optical system of the medical observation device;
determine a parameter based on a type of a scope of the medical observation device after a change occurs and a table obtained in advance and represents a relationship between the type of scope and the parameter; and
set a generation condition of three-dimensional information based on the medical field data by using a determination result.

18. A medical observation device comprising:
an imaging sensor configured to image a medical field and generate medical field data; and
a display configured to output the medical field data, the medical observation device being used in a medical observation system in which a change in an optical system of the imaging sensor is detected, in a case where a change in the optical system is detected, divide the medical field data for each section that is a segment including frames of a plurality of medical field images based on the change in the optical system, a parameter for each section determined depending on the optical system after the change and a type of a scope of the medical observation is determined, and a generation condition of three-dimensional information based on the medical field data is set by using a determination result.

19. The medical observation device according to claim 18, wherein the display is configured to display a detection result of a change in the optical system.

20. The medical observation device according to claim 18, wherein the display is configured to display the three-dimensional information before a change and the three-dimensional information after a change.

* * * * *